United States Patent [19]
Bombardelli et al.

[11] Patent Number: 5,843,910
[45] Date of Patent: Dec. 1, 1998

[54] COLCHICINE DERIVATIVES AND THE THERAPEUTICAL USE THEREOF

[75] Inventors: Ezio Bombardelli; Bruno Gabetta, both of Milan, Italy

[73] Assignee: Indena S.p.A., Milan, Italy

[21] Appl. No.: 817,626

[22] PCT Filed: Sep. 27, 1995

[86] PCT No.: PCT/EP95/03823

§ 371 Date: Mar. 21, 1997

§ 102(e) Date: Mar. 21, 1997

[87] PCT Pub. No.: WO96/11184

PCT Pub. Date: Apr. 18, 1996

[30] Foreign Application Priority Data

Oct. 5, 1996 [IT] Italy .................................. MI94A2026

[51] Int. Cl.$^6$ ........................ A61K 31/70; A61K 31/16; C07H 15/00; C07C 321/00
[52] U.S. Cl. ............................. 514/33; 514/629; 536/4.1; 536/17.9; 560/10; 560/28
[58] Field of Search ....................... 514/33, 629; 536/4.1, 536/17.9; 560/10, 28

[56] References Cited

FOREIGN PATENT DOCUMENTS 0 356 137  2/1990  European Pat. Off. .
1 221 142  2/1971  United Kingdom .
1 345 991  2/1974  United Kingdom .

OTHER PUBLICATIONS

Liebigs Annalen Der Chemie, vol. 758, 12 Jul. 1972 Weinheim, DE. pp. 185–189, H. Lettre, et al.

Journal of Medicinal Chemistry, vol. 24, No. 3, Mar. 1981 Washington, DC pp. 251–256, F.R. Quinn et al.

Journal of Medicinal Chemistry, vol. 36, No. 5, 5 Mar. 1993 Washington, DC U.S. pp. 554–551, L.Sun et al.

*Primary Examiner*—Elli Peselev
*Attorney, Agent, or Firm*—Pennie & Edmonds

[57] ABSTRACT

The present invention relates to novel colchicine derivatives of formula (1), where Y is a —$CH_2$—CH—NH—$R_3$ group or a —CH—$CH_2OR_3$ group and the other variables are as defined in claim 1, having antiproliferative, antitumoral and anti-inflammatory activities. The novel compounds have a cytotoxicity on human tumoral cell lines comparable with colchicine, but, in comparison with the latter, they are less toxic and more selective, particularly on cells resistant to the usual medicaments. Some compounds have a marked activity on TNF and interleukine 2, and therefore are very potent anti-inflammatory agents. They can be included in pharmaceutical formulations useful for the parenteral, oral and topical administrations.

18 Claims, No Drawings

COLCHICINE DERIVATIVES AND THE THERAPEUTICAL USE THEREOF

TECHNICAL FIELD

The present invention relates to novel colchicine derivatives having antiproliferative, antitumoral and antiinflammatory activities, the methods for the preparation thereof and the pharmaceutical formulations containing them.

BACKGROUND OF THE INVENTION

Colchicine is a known pseudo-alkaloid widely used for a very long time in therapy for the treatment of gout; it acts very quickly and specifically, even though it should be used for short times due to its toxicity. In addition, colchicine is a very potent antiblastic agent, whose action is connected with a mechanism blocking the formation of the mitotic spindle in cell division; this latter aspect has been investigated thoroughly for any antitumoral activity and a great deal of colchicine derivatives have been prepared for this purpose.

Colchicine as such and a number of its prepared derivatives cannot be used due to its high toxicity in terms of risk/benefit ratio. Only one colchicine derivative, demecolcine, is used in some degree in oncology for the treatment of some leukemia forms. As far as the use in the antiinflammatory field is concerned, the only marketed colchicine derivative is thiocolchicoside, bearing a thiomethyl moiety at $C_{10}$ and a glucose molecule at the hydroxyl in $C_3$; the therapeutical uses of this derivative are related to the muscle relaxant and antiphlogistic effects. The products of the invention differ from those of the prior art in the high therapeutical index. In the antitumoral field, researches have been focused on the research of products having, besides a normal cytotoxicity, a cytotoxicity aimed at cell lines resistant to the usual antiblastic medicaments.

SUMMARY OF THE INVENTION

The derivatives of the present invention have the general formula 1

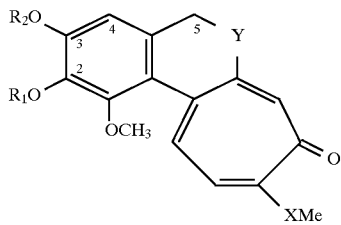

wherein:

X can be an oxygen or sulfur atom;

$R_1$ and $R_2$, which can be the same or different, are straight or branched alkyl groups or cycloalkyl groups, containing 1 to 6 carbon atoms; or saturated or unsaturated acyl groups, containing 16 to 22 carbon atoms, or a β-D-glucose residue as such or a β-D-glucose residue wherein the hydroxyl in positions 4 and 6 are protected as chetals with aliphatic or aromatic or heteroaromatic aldehydes; Y is a —$CH_2$—CH—NH—$R_3$ group, the methylene group of which being bound to the carbon in position 5 and the methine group, having the same absolute configuration as colchicine, is bound to the tropolone ring, or a —CH—$CH_2OR_4$ group, the methine group of which being bound to the carbon in position 5 and to the tropolone ring and having absolute configuration S;

$R_3$ is an acyl group containing 2 to 6 carbon atoms bearing one to three halogen atoms, preferably fluorine or chlorine, or an acyl group from a natural amino acid, wherein the amino group can be free or protected as trifluoroacetamide or benzamide;

$R_4$ is an acyl residue of a dicarboxylic acid containing 4 to 6 carbon atoms, or an acyl residue of a natural amino acid, wherein the colchicine amino group can be free or protected as trifluoroacetamide or benzamide, or a glycoside residue consisting of D-glucose, D-galactose, L-fucose or L-rhamnose. In this case, the sugars act as chemotactic for melanocytes, hepatocytes, fibroblasts or they give the derivative the characteristic of a pro-drug.

Preferred compounds of formula 1 are those wherein X is sulfur.

$R_1$ and $R_2$, which are the same or different, are preferably hydrogen or $C_1$–$C_6$ alkyl.

Y is preferably a group of formula —$CH_2$—CH—$NHR_3$ as defined above.

DETAILED DESCRIPTION OF THE INVENTION

For the preparation of the products of the invention, the starting products used are the natural substances colchicine (1; X=O; $R_1$=$R_2$=Me; Y=$CH_2$—CH—NHAc), 2-O-demethylcolchicine (1; X=O; $R_1$=H; $R_2$=Me; Y=$CH_2$—CH—NHAc), 3-O-demethylcolchicine (1; X=O; $R_1$=Me; $R_2$=H; Y=$CH_2$—CH—NHAc), colchicoside (1; X=O; $R_1$=Me; $R_2$=β-D-glucose; Y=$CH_2$—CH—NHAc) which can be recovered from vegetable materials according to procedures known in literature. These natural substances, by treatment with methylmercaptan in alkali solution, according to procedures also known in literature, yield the corresponding thioderivatives which are used as the syntones for the preparation of the derivatives of general formula 1, wherein X is sulfur.

For the preparation of the derivatives of general formula 1 wherein $R_1$ and $R_2$ are alkyl or acyl groups, the starting products used are the colchicine or thiocolchicine syntons demethylated in position 2 or 3. These syntons are subjected to alkylation or acylation using the well known methods for the phenol derivatization. Analogously, the derivatives of general formula 1 wherein $R_1$ or $R_2$ are a β-D-glucose residue or a β-D-glucose residue wherein the hydroxyls in 4 and 6 are protected as chetals with aliphatic or aromatic aldehydes, are prepared from colchicine or thiocolchicine syntons demethylated in position 2 or 3. These syntons are subjected to a reaction with α-bromotetraacetyl-D-glucose or with 2,3-di-O-dichloroacetyl-β-D-glucose containing a chetal group involving the hydroxyls in the positions 4 and 6 (cf. Canada Pat. N. 956939). After removing the protective acyl groups by known methods described in literature, the derivatives glucosidated in the position 2 or 3 according to the present invention are obtained.

The derivatives of formula 1 wherein Y is a —$CH_2$—CH—NH—$R_3$ group are prepared subjecting to N-desacetylation by acid catalysis the colchicine or thiocolchicine syntons, bearing methoxy or hydroxy groups in the positions 2 and 3, followed by acylation of the primary amino moiety with an acid reactive derivative containing one to three fluorine or chlorine atoms or a natural amino acid, the amino group of which can be free or protected as trifluoroacetamide or benzamide. The derivatives of formula 1 wherein $R_3$ has the meaning defined above are thereby prepared. The derivatives of formula 1 wherein Y is a —CH—CH$_2$—OR$_4$ group are obtained subjecting colchicine or thiocolchicine syntons, bearing methoxy or hydroxy groups in positions 2 and 3, to N-desacetylation followed by treatment with sodium nitrite and acetic acid which contracts of the cycloheptane ring with the formation of the syntons of formula 1 wherein Y=—CH—CH$_2$OH (J. Med. Chem. 36, 544, 1993). The resulting primary alcohol moiety yields, by reaction with suitably activated dicarboxylic acids, or with activated natural amino acids, wherein the amino group can be free or protected as trifluoroacetamide or benzamide, or with the reactive form of the sugars D-glucose, D-galactose, L-fucose or L-rhamnose, the derivatives of general formula 1 wherein Y=CH—CH$_2$OR$_4$, R$_4$ having the meaning defined above.

The following table shows the antimitotic activity on tumoral cell lines of some derivatives of the invention. Taxol and colchicine are the comparison substances.

TABLE

In vitro cytotoxic activity of some novel colchicine derivatives.

| Substances | IC$_{50}$ (nM) Cell lines | | | | |
|---|---|---|---|---|---|
| | Ovary | Colon | Breast | Lung | Cell. resist. |
| Taxol | 6.1 | 3.5 | 3.2 | 1.7 | 299 |
| Colchicine | 5.3 | 3.9 | 4.4 | 16 | 112 |
| Compound IZ | 4.2 | 2.6 | 6.2 | 8 | 26 |
| Compound IIZ | 9.4 | 1.8 | 5.0 | 19 | 11 |
| Compound IVZ | 6.1 | 2.2 | 4.1 | 12 | 7 |

This table evidences that the novel derivatives have significant advantages on the resistant cell lines, which is the main target for cytotoxic medicaments. The products of the present invention can be incorporated in pharmaceutical formulations useful for the administration of the medicament. Formulations for the parenteral, oral, transdermal, epicutaneous administrations can be conveniently prepared.

Among the excipients useful to prepare said formulations, natural and synthetic phospholipids proved to be particularly useful for preparing liposomial forms for the parenteral, transdermal or epicutaneous routes; the latter two formulations being particularly useful in the treatment of arthrosic or peripheral venous inflammatory conditions; said formulations also being useful in the topical treatment of cutaneous epitheliomas and in cutaneous hyperproliferative conditions, such as psoriasis. In the specific antitumoral field, besides the phospholipids which allow for the administration of the medicament in liposomial form, some surfactants such as polyethoxylated castor oil, such as for example Cremoform L50, or polisorbate, such as for example Tween, acting synergistically with the active ingredient, turned out to be particularly useful. In oncology, the products are used at dosages from 1 to 100 mg/m$^2$, whereas as antiinflammatory the dosages range from 1 to 20 mg per unit dose, one to more times daily. All of the pharmaceutical formulations such as vials, capsules, creams etc. can be prepared with the main part of said derivatives.

EXAMPLES

The following examples further illustrate the invention.

Example I

Preparation of N-desacetyl-N-trifluoroacetyl-3-O-demethyl-3-O-cyclopentyl-thiocolchicine, compound IZ (1; X=S; R$_1$=Me; R$_2$=C$_5$H$_9$; Y=CH$_2$CHNH—COCF$_3$).

20 g of 3-O-demethylthiocolchicine (1; X=S; R$_1$=Me; R$_2$=H; Y=CH$_2$CHNHAc) are dissolved in 300 ml of 20% sulfuric acid and treated at 100° C. under nitrogen atmosphere for 36 h. The reaction mixture is neutralized, thus separating 12 g of N-desacetyl-3-O-demethylthiocolchicine (1;X=S; R$_1$=Me; R$_2$=H; Y=CH$_2$CHNH$_2$). This product is dissolved in acetone and reacted with 3 equivalents of trifluoroacetic anhydride under strong stirring in the presence of anhydrous Na$_2$CO$_3$. After 2 h the reaction mixture is filtered and the solution is evaporated to dryness. The residue, consisting of 3-O-demethyl-N,3-O-bistrifluoroacetylthiocolchicine, is hydrolysed in methanol containing NH$_4$Cl. The reaction mixture is evaporated to dryness under vacuum and the residue taken up in acetone. The acetone solution is filtered and refluxed for eight hours with 5 equivalents of cyclopentyl bromide in the presence of sodium carbonate. Salts are filtered off, the solution is evaporated to dryness and the residue is purified by chromatography on silica gel column using ethyl acetate as eluent. By crystallization from acetone/hexane. 8.6 g of product are obtained, M$^+$a m/z 523.

Example II

Preparation of N-desacetyl-N-trifluoroacetyl-3-O-demethyl-3-O-isopropyl-thiocolchicine, compound IIZ (1; X=S; R$_1$=Me; R$_2$=iPr; Y=CH$_2$—CH—NHCOCF$_3$).

For the preparation of this derivative, the procedure of example I is repeated, using as reagent isopropyl bromide instead of cyclopentyl bromide. After purification of the crude reaction product on silica gel and crystallization, 7.6 g of product are obtained, M$^+$a m/z 497.

Example III

Preparation of N-desacetyl-N-trifluoroacetylthiocolchicoside, compound IIIZ (1; X=S; R$_1$=Me; R$_2$=β-D-glucosyl; Y=CH$_2$—CH—NHCOCF$_3$).

10 g of N-desacetyl-thiocolchicoside (1; X=S; R$_1$=Me; R$_2$=β-D-glucose; Y=CH$_2$—CH—NH$_2$) are dissolved in acetone and treated for two hours at 10° C. with three equivalents of trifluoroacetic anhydride. The mixture is evaporated to dryness and the residue is crystallized from isopropanol and subsequently from ethanol. 8.5 g of product are obtained, M$^+$a m/z 617.

Example IV

Preparation of N-(N-trifluoroacetyl-α-phenylglycyl)-desacetylthiocolchicine, compound IVZ (1; X=S; R$_1$=R$_2$=Me; Y=CH$_2$—CH—NH—CO—CH(NHCOCF$_3$)Ph).

400 mg of N-desacetyl-thiocolchicine (1; X=S; R$_1$=R$_2$=Me; Y=CH$_2$—CH—NH$_2$) (1.07 mmol) are dissolved together with 265 mg (1,07 mmol) of L-N-trifluoroacetyl-α-phenyl-glycine in 10 ml of methylene chloride under nitrogen atmosphere. The solution is added 221 mg (1.07 mmol) of N,N-dicyclohexylcarbodiimide, stirring until disappearance of the reagents. The reaction mixture is cooled to −30° C. and filtered to remove the precipitated urea. The chloromethylene solution is concentrated and purified by filtration on silica gel eluting with a methylene chloride/methanol 98:2 mixture. Upon crystallization from methylene chloride/ethyl ether, 350 mg of product are obtained, M$^+$a m/z 602.

Example V

Preparation of N-(N-trifluoroacetyl-L-alanyl)-desacetylthiocolchicine, compound VZ (1; X=S; R$_1$=R$_2$=Me; Y=CH$_2$—CH—NH—CO—CH(NHCOCF$_3$)CH$_3$).

400 mg of N-desacetyl-thiocolchicine (1,07 mmol) are treated with one equivalent of N-trifuoroacetyl-L-alanine and one equivalent of N,N-dicyclohexylcarbodiimide in 10 ml of methylene chloride and under nitrogen atmosphere until disappearance of the reagents. The reaction mixture is cooled to –30 ° C. and filtered to remove the precipitated urea. The chloromethylene solution is concentrated and purified by filtration on silica gel eluting with a methylene chloride/methanol 98:2 mixture. Upon crystallization from methylene chloride/ethyl ether, 94 mg of product are obtained, $M^+$a m/z 540.

Example VI

Preparation of N-(N-trifluoroacetylmethionyl)-desacetylthiocolchicine, compound VIZ (1; X=S; $R_1=R_2=Me$; Y=$CH_2$—CH—NHCO—CH(NHCOCF$_3$)CH$_2$—CH$_2$—SMe).

The procedure of example IV is repeated, reacting N-trifluoroacetylmethionine. By fractional crystallization, upon chromatographic purification of the reaction residue, from 400 mg of N-desacetylthiocolchicine, 84 mg of product are obtained, $M^+$a m/z 600.

Example VII

Preparation of N-(α-phenylglycyl)desacetylthiocolchicine, compound VIIZ (1; X=S; $R_1=R_2=Me$; Y=$CH_2$—CH—NHCO—CHNH$_2$—Ph).

400 mg of the product obtained in example IV are dissolved in 5 ml of 50% acetone in the presence of 120 mg of potassium carbonate and heated at 60° C. with stirring for 5 hours. The reaction mixture is cooled, saturated with NaCl and extracted with chloroform. The organic phase is dried over anhydrous sodium sulfate, then concentrated to dryness and the residue is chromatographed on silica gel with a methylene chloride/methanol 98:2 mixture. 160 mg of product are obtained, $M^+$a m/z 506.

Example VIII

Preparation of N-desacetyl-N-trifluoroacetyl-3-O-demethyl-3-O-ximeninylthiocolchicine, compound VIIIZ (1; X=S; $R_1$=Me; $R_2$=CO(CH$_2$)$_7$C≡C—CH=CH—(CH$_2$)$_5$CH$_3$; Y=$CH_2$—CH—NH—CO—CF$_3$).

500 mg of N-desacetyl-N-trifluoroacetyl-3-O-demethylthiocolchicine (1; X=S; $R_1$=Me; $R_2$=H; Y=$CH_2$—CH—NHCOCF$_3$) are dissolved in 2.5 ml of pyridine and added at 0° C. with 500 mg of ximeninic acid chloride. The reaction mixture is left to stand overnight at room temperature, then is poured onto ice. The resulting precipitate is separated and crystallized from da acetone/hexane, $M^+$a m/z 715.

Example IX

Preparation of 5,6-dihydro-6(S)-[(β-D-glucopyranosyloxy)methyl]-1,2,3-trimethoxy-9-(methylthio)-8H-cyclohepta[a]naphthalen-8-one, compound IXZ (1; X=S; $R_1=R_2=Me$; Y=CH—CH$_2$-β-D-glucose).

10 g of N-desacetylthiocolchicine are treated with sodium nitrite to give 4 g of 5,6-dihydro-6(S)-(hydroxymethyl)-1,2,3-trimethoxy-9-methylthio-8H-cyclo-hepta[a]naphthalen-8-one, according to the process described in J. Med. Chem., 36, 544, 1993. The resulting product is treated for 12 hours under reflux in acetonitrile with 26 g of α-bromotetraacetylglucose in the presence of 85 g of mercuric cyanide. Salts are filtered off and the solution is evaporated to dryness, taken up with 70% acetone and treated for two hours with 15% sodium carbonate. The mixture is neutralized, extracted with ethyl acetate and chromatographed on silica gel eluting with a methylene chloride-ethanol 9:1 mixture. 2.1 g of product are obtained, $M^+$a m/z 536.

Example X

Preparation of 5,6-dihydro-6-(S)-(hydroxymethyl)-1,2,3-trimethoxy-9-(methylthio)-8H-cyclohepta-[a]naphthalen-8-one succinyl ester, compound XZ (1; X=S; $R_1=R_2=Me$; Y=CH—CH$_2$—OCOCH$_2$CH$_2$CO$_2$H).

10 g of N-desacetylthiocolchicine are treated as in example IX. The resulting naphthalen-8-one is dissolved in pyridine and treated under reflux for 24 hours with a succinic anhydride excess. The reaction mixture is cooled, poured into abundant water and extracted with methylene chloride. The organic phase is concentrated to small volume and purified on silica gel eluting with a methylene chloride-water-methanol 70:30:5 mixture. After crystallization from methanol, 7 g of product are obtained, $M^+$a m/z 474.

What is claimed is:

1. A colchicine compound of formula 1

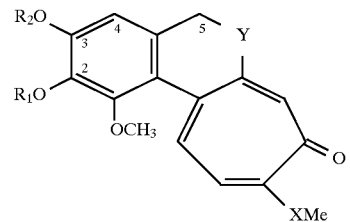

wherein:

X is an oxygen or sulfur atom;

$R_1$ and $R_2$, which can be the same or different, are straight or branched alkyl groups or cycloalkyl groups, containing 1 to 6 carbon atoms; or saturated or unsaturated acyl groups, containing 16 to 22 carbon atoms, or a β-D-glucose residue as such or β-D-glucose residue wherein the hydroxyls in positions 4 and 6 are protected as chetals with aliphatic or aromatic or heteroaromatic aldehydes; Y is a —CH$_2$—CH—NH—R$_3$ group, the methylene group of which being bound to the carbon in position 5 and the methine group, having the same absolute configuration as colchicine, is bound to the tropolone ring, or a —CH—CH$_2$OR$_4$ group, the methine group of which being bound to the carbon in position 5 and to the tropolone ring and having absolute configuration S;

$R_3$ is an acyl group containing 2 to 6 carbon atoms bearing one to three halogen atoms, or an acyl group from a natural amino acid, wherein the amino group can be free or protected as trifluoroacetamide or benzamide with the proviso that when R1 and R2 are methyl, X is an oxygen or sulfur atom, and R3 is not —COCH$_2$F, —COCH$_2$Cl, or —COCH$_2$Br, or —COCH$_2$I;

when R1 and R2 are methyl, X is an oxygen atom, and R3 is not —COCl$_3$, —COCHCl$_2$, —COCHF$_2$, —COCH$_2$CHClCH$_3$; or —COCH$_2$CH$_2$CHBrCH$_3$;

$R_4$ is an acyl residue of a dicarboxylic acid containing 4 to 6 carbon atoms, or an acyl residue of a natural amino acid, wherein the amino group can be free or protected as trifluoroacetamide or benzamide, or a glycoside residue consisting of D-glucose, D-galactose, L-fucose or L-rhamnose.

2. The colchicine compound according to claim 1, wherein X is sulfur.

3. The colchicine compound according to claim 1, wherein X is oxygen.

4. The colchicine compound according to claim 1, wherein $R_1$ and $R_2$, which are the same or different, are straight or branched alkyl groups or cycloalkyl groups containing 1 to 6 carbon atoms.

5. The colchicine compound according to claim 1, wherein Y is a group of formula $-CH_2-CH-NH-R_3$ as defined in claim 1.

6. Pharmaceutical composition containing as active ingredient a compound of claim 1 in admixture with a suitable carrier.

7. The colchicine compound of claim 1 wherein $X=S$, $R_1=CH_3$; $R_2=C_5H_9$; and $Y=CH_2CHNH-COCF_3$.

8. The colchicine compound of claim 1 wherein $X=S$; $R_1=CH_3$; $R_2=$isopropyl; and $Y=CH_2-CH-NHCOCF_3$.

9. The colchicine compound of claim 1 wherein $X=S$; $R_1=CH_3$; $R_2=$B-D-glucose; and $Y=CH_2-CH-NH_2$.

10. The colchicine compound of claim 1 wherein $X=S$; $R_1$ and $R_2=CH_3$ and $Y=CH_2-CH-NH-CO-CH(NHCOCF_3)Ph$.

11. The colchicine compound of claim 1 wherein $X=S$; $R_1$ and $R_2=CH_3$; and $Y=CH_2-CH-NH-CO-CH(NHCOCF_3)CH_3$.

12. The colchicine compound of claim 1 wherein $X=S$; $R_1$ and $R_2=CH_3$; and $Y=CH_2-CH-NHCO-CH(NHCOCF_3)CH_2-CH_2-CH_3$.

13. The colchicine compound of claim 1 wherein $X=S$; $R_1$ and $R_2=CH_3$; and $Y=CH_2-CH-NHCO-CHNH_2-Ph$.

14. The colchicine compound of claim 1 wherein $X=S$; $R_1=CH_3$; $R_2=CO(CH_2)_7C=C-CH=CH-(CH_2)_5CH_3$ and $Y=CH_2-CH-NH-NH-CO-CF_3$.

15. The colchicine compound of claim 1 wherein $X=S$; $R_1$ and $R_2=CH_3$; and $Y=CH_2-$B-D-glucose.

16. The colchicine compound of claim 1 wherein $X=S$; $R_1$ and $R_2=CH_3$; and $Y=CH-CH_2-OCOCH_2CH_2CO_2H$.

17. A method for imparting anti-proliferative, anti-tumoral or anti-inflammatory activity in a subject in need of same, which comprises administering to the subject a colchicine compound according to claim 1 in an amount which is therapeutically effective to obtain the anti-proliferative, anti-tumoral or anti-inflammatory activity.

18. The pharmaceutical composition of claim 6 wherein the carrier is a phospholipid.

* * * * *